United States Patent [19]

Perry et al.

[11] Patent Number: 5,087,338
[45] Date of Patent: Feb. 11, 1992

[54] PROCESS AND DEVICE FOR SEPARATING ELECTRICALLY CHARGED MACROMOLECULAR COMPOUNDS BY FORCED-FLOW MEMBRANE ELECTROPHORESIS

[75] Inventors: Mordechai Perry, Petach Tikva; Jack Gilron, Rehovot; Reuven Ketraro, Rishon Letzion; Charles Linder, Rehovot, all of Israel

[73] Assignee: Aligena AG, Basel, Switzerland

[21] Appl. No.: 435,837

[22] Filed: Nov. 14, 1989

[30] Foreign Application Priority Data

Nov. 15, 1988 [GB] United Kingdom ............... 8826661

[51] Int. Cl.$^5$ .............................................. B01D 13/02
[52] U.S. Cl. ................................. 204/182 B; 204/306; 204/301
[58] Field of Search ................ 204/182.3, 306, 301

[56] References Cited

U.S. PATENT DOCUMENTS

| 3,870,617 | 5/1975 | Bourat | 204/182.3 |
| 3,972,791 | 8/1976 | Stern | 804/182.1 |
| 3,989,613 | 11/1976 | Gritzner | 204/182.3 |
| 4,043,895 | 8/1977 | Gritzner | 204/301 |
| 4,146,455 | 3/1979 | McRae | 204/182.6 |
| 4,673,483 | 6/1987 | Mandle | 204/301 |
| 4,758,320 | 7/1988 | Sanchez | 204/182.3 |
| 4,830,720 | 5/1989 | Harada et al. | 204/131 |

FOREIGN PATENT DOCUMENTS

| 1223635 | 6/1960 | France . |
| WO79/00942 | 11/1979 | PCT Int'l Appl. . |
| 936805 | 9/1963 | United Kingdom . |
| 1338543 | 11/1973 | United Kingdom . |

Primary Examiner—John Niebling
Assistant Examiner—Arun S. Phasge
Attorney, Agent, or Firm—Wenderoth, Lind & Ponack

[57] ABSTRACT

A process and apparatus for the continuous separation of electrically charged macromolecular compounds, such as proteins, by forced-flow membrane electrophoresis is provided.

Said process is conducted in an electrophoretic cell comprising a membrane compartment, divided by a micro- or ultrafiltration membrane into a feed and permeate cell, and electrode compartments being partitioned from the membrane compartment with ion-exchange membranes, which are impermeable to the macromolecular compounds, and have virtually no permeability to salts.

The electrophoretic process comprises the steps of recycling a mixed solution of the charged compounds which are dissolved in a separation buffer through the feed cell, subjecting of the solution to a pressure-driven membrane separation, applying an electric field across the membranes and the solution to cause electrophoretic migration of the charged compound and to separate them, and withdrawing the charged compounds thus separated.

The process achieves separation of charged compounds having differences of their isoelectric points in a range of as low as 0.1 to 0.2. The process is very useful to remove charged contaminants from the desired compounds.

13 Claims, 4 Drawing Sheets

FIG. 2

PROCESS AND DEVICE FOR SEPARATING ELECTRICALLY CHARGED MACROMOLECULAR COMPOUNDS BY FORCED-FLOW MEMBRANE ELECTROPHORESIS

The present invention relates to separation of electrically charged macromolecular compounds utilizing electrophoretic migration by forced-flow membrane electrophoresis in a continuous manner.

Forced-flow membrane electrophoresis is a term originally coined in U.S. Pat. No. 2,878,178 for a separation technique which is effected by passing solutions or suspensions of electrically charged macromolecular compounds, e.g. colloidal biopolymers, such as proteins, under pressure parallel to a microporous membrane which divides an electrophoretic unit into two chambers. A portion of the fluid is forced through the membrane and protein molecules are carried through with the fluid. An electric field is applied perpendicular to the membrane and parallel to the permeate flux, with a polarity such that proteins which are appropriately charged (e.g. all those with an isoelectric point (pI) higher than the pI of a target molecule to be separated) are given an electrophoretic velocity opposite to that of the permeate flux and retained on the feed side while the target protein is swept through to the permeate side in more purified form.

However, the importance of a tangential recycling flow on the feed and the permeate sides on the separation efficiency was not realized and not mentioned elsewhere. On the contrary, very low circulation flows were used in order to maintain a gravitationally stable flow profile in the cells. The range of circulation flow rates parallel to the membrane were kept below 0.01 cm/sec. Nevertheless, the separations which could be demonstrated in the small scale devices were not very sharp. In the upscaled commercial installations, a large number of parallel cells with large membrane area must be incorporated. It may be difficult to guarantee identical flow profiles in each compartment of the large scale devices and therefore the expected separation will be lower than that demonstrated so far.

A variation has been described in U.S. Pat. No. 3,989,613 in which a buffer solution is pumped parallel to the membrane on the permeate side as well to help sweep away the target molecules which permeate through the membrane. There is, however, no net transfer of fluid from one compartment to the other. Instead, only the appropriately charged species is carried over electrophoretically.

In both of these devices the recycle rate parallel to the membrane was very slow (<0.01 cm/s). On the other hand, as much as 50% of the fluid would pass through the filter per pass through the device. In such cases significant electric polarization effects could be encountered.

In all of the known devices for forced flow electrophoresis, dialysis membranes were used to separate the electrode compartments from the filter (membrane) compartments. At the high field strengths needed, acid and base are generated at the anode and cathode respectively, and contaminate the neighboring solution causing a change in pH if the buffer is exhausted. To prevent this, high concentrations of buffer must be used which raise the conductivity to very high levels and thus require higher currents to maintain the same field strength.

It can be shown that the volume of purified permeate passed per unit of charge passed across the membrane is given by the ratio of the electrophoretic mobility to the specific conductivity of the solution. Therefore, and also in order to minimize Joule-heating of the feed solution, it is more energy efficient to work at the lowest conductivities possible.

Also if the voltage is too high the dialysis membranes used to protect the electrodes from the process streams can be fouled, leading to a loss of flux. As illustrated in U.S. Pat. No. 3,989,613, in the absence of strong tangential flow in the device electric polarization occurs at membranes protecting the electrode solutions, causing excessive voltage drops to maintain the current density required for a particular field strength. This polarization arises from the absence of strong tangential flow on the permeate side and/or the feed side of the microporous membrane filter.

The replacement of the non-conducting dialysis membrane with the ion-exchange membrane on the boundary between the electrode and separating cells, which is one of the inventive embodiments, helps to prevent the fouling due to absorbed proteins. This will be explained in the following. During the passage of electric current water splitting occurs on the surface of the ion-exchange membranes. The effect is predominant when dilute solutions and high current density are used. During the water splitting the protons or hydroxyl ions are removed from the feed or permeate side causing pH barriers to accumulate on both surfaces of the ion-exchange membranes. For example anion-exchange membranes remove hydroxyl ions towards the anode. The surface contacting the protein solution maintains a local acid layer. Negatively charged proteins, which are attracted to the anode will meet on the anion-exchange membrane facing the feed side, the acid layer. The original negative charge will be neutralized and changed to positive. As a result the protein will be repelled from the anion-exchange membrane toward the cathode. Similar effect will occur at the cation-exchange membrane in the permeate cell. This is the mechanism by which membrane fouling is eliminated.

As described hereinbefore the known forced-flow membrane electrophoresis processes suffer from various disadvantages which can be summarized as follows:

leakage of acids and bases formed at the electrodes that enter the membrane cell and change the pH-value of the feed mixture, thereby the sensitivity to remixing from natural connection due to Joule-heating, which causes the drop of the separability of the macromolecular compounds;

the electric polarization in the electrophoretic cell;

and the insufficient resolution of the compound mixtures achieving a range of differences in isoelectric point of about ±1.0 only.

It was now found that most of these disadvantages can be overcome by a substantial new and improved separation method for electrically charged macromolecular compounds using forced-flow membrane electrophoresis.

Therefore, a principal object of the present invention is to provide a process for the continuous separation of electrically charged macromolecular compounds by forced-flow membrane electrophoresis, which comprises conducting said process in an electrophoretic cell comprising (1) a membrane compartment consisting of a feed and a permeate cell which are divided by a micro- or ultrafiltration membrane permeable to said macromolecular compound, (2) at both sides thereto electrode compartments being partitioned from the cells of the membrane compartment with ion-exchange membranes, being impermeable to said macromolecular compounds and having no or very low permeability to salts, and (3) means to control the flow rate of the permeate, by the process steps of (a) recycling aqueous solutions containing mixtures of electrically charged macromolecular compounds, and having a pH-value between the isoelectric points of said macromolecular compounds, through said feed cell and subjecting them to a pressure-driven membrane separation treatment, (b) simultaneously applying an electric field across the solutions and the membranes to induce electrophoretic migration of at least one of the macromolecular compounds through the micro- or ultrafiltration membrane or away from the membranes, (c) adjusting the flow rate of the permeate to a predetermined value, (d) withdrawing at least one of the macromolecular compounds either from the feed or permeate cell, and (e) recycling a dilute buffer solution through the permeate cell to sweep away macromolecular materials which have permeated through the membranes; the dilute solution may be at a pH equal to or lower or higher than the pH of the feed solution, the recycle rate in the permeate and feed cells being many times the rate of feed solution-permeation and the residence time of the solution in the cells being very short.

Another object of the invention is to provide an apparatus suitable to carry out said forced-flow membrane electrophoresis. In general terms this apparatus comprises electrode cells spaced from each other and having the anode and cathode located therein, a membrane compartment of a feed and a permeate cell being divided by a micro- or ultrafiltration membrane permeable to electrically charged macromolecular compounds, being located between said electrode cells and partitioned therefrom with ion-exchange membranes impermeable to said macromolecular compounds, and having no or very low permeability to salts, an inlet for supplying the aqueous solutions containing the electrically charged macromolecular compounds into the feed cell of the membrane compartment, an inlet for supplying buffer solution to sweep through the permeate cell of the membrane compartment, inlets and outlets for electrolyte (buffer) and washing liquid circulation which are pumped through the anode and cathode compartment, outlets for withdrawing (a) separated solution(s) of the macromolecular compounds and by-products, means for controlling the permeate flow rate at a predetermined rate, means for maintaining a constant predetermined permeation rate, and other means, including pumps for supplying and circulating the aqueous solutions, storage tanks and monitoring devices (for details of this apparatus reference is made to FIG. 2).

Other objects of the present invention will become apparent from the following description and the drawings of this specification.

In forced-flow membrane electrophoresis the fluid flow used to move the different macromolecular compounds (proteins) at different rates parallel to the electric field is done by cycling the fluid perpendicular to the electric field while the pressure forces part of the fluid in a direction parallel to the field across a separating semipermeable membrane. Forced flow electrophoresis has an advantage over free flow zone electrophoresis in that the sample need not be injected at a particular point and the problem of diffusive spreading of the separated zones is eliminated. Forced-flow electrophoresis, however, has a higher capacity and lower residence times which are only limited by the electric field strength needed to balance the permeate flux through the membrane.

The electrophoretic velocity is given by the relation $$V = u \cdot E \quad (1)$$

where u is the electrophoretic mobility (in $cm^2$/Volt sec.) of the charged compound and is a function of pH. Therefore the quality of separation resolution depends on control of the pH, permeate flow, and operating field strengths. E (in Volt/cm) is the electric field strength and is proportional to the current density ($A/cm^2$) and inversely proportional to the specific conductivity of the feed solution. The power dissipated in these units per unit area is proportional to the distance between the electrodes (hence thickness of the flow passage) and the square of the current density. Hence to minimize Joule-heating of the feed solution there is a premium on maintaining flow channels of minimum thickness and feed and permeate solutions of minimum conductivity so that a given field strength can be maintained with a minimum current density.

In the case where very sharp separations are required, especially when separating between colloidal components characterized with very low and close electrophoretic mobilities, it is essential to perform the separation at very high field intensities. The localization of the field intensity to the region of the separating cells only (feed and permeate) will minimize Joule-heating-/cooling problems and sharpen the separation.

This option can be effectively achieved by operating the membrane cells (feed and permeate cell) with very low buffer concentrations, while keeping the concentration of the electrolyte in the adjacent electrode compartment at a relatively high value.

To achieve the required combination of conditions it would be very desirable to separate the electrode compartments from the separating (membrane) cells by means of an ion conducting membrane impermeable to salt and macromolecular compounds. Such set up would enable one to create electrical contact throughout the cells, while preventing salt leakage from the electrode compartments. It is thus possible to use highly concentrated electrolyte in the electrode compartment in contact with very dilute buffer solutions in the colloid separating cells. This option is contrasting the usually applied configurations based on a salt permeable, non-conducting dialysis membrane, which in the present invention is replaced with a salt impermeable ion-exchange membrane.

In the following detailed description of the invention reference is made to the figures of the drawings. The numbers refer to the parts of the figures.

FIG. 3 schematically shows the flow of electrically charged compounds when subjected to the inventive forced-flow membrane electrophoresis.

This modified apparatus is a further object of the present invention.

The principle of the present invention is described with reference to FIG. 1. The apparatus for carrying out the inventive forced-flow membrane electrophoresis can be of a flat, cylindrical or spiral wound geometry with a flow passage divided by a microporous membrane (1) (which is a micro- or ultrafiltration membrane permeable to electrically charged macromolecular compounds) into a high pressure (2) (feed cell) and low pressure (3) side (permeate cell). This flow passage is situated between a pair of electrodes (anode 4 and cathode 5) in corresponding electrode compartments (6) and (7) which are partitioned from the high/low pressure side of the membrane by ion-exchange membranes: an anion-exchange membrane (8) is bordering the anode compartment (6) and a cation-exchange membrane (9) is bordering the cathode compartment (7).

The electrodes (4 and 5) generate an electric field across the flow passage.

The ion-exchange membranes (8 and 9) can be of any of the commercial types available, provided they allow little or no passage of neutral salts or other uncharged molecules. This would include but not be limited to intrinsic ion-exchange membranes and also ion-exchange resins embedded in another polymer membrane matrix. The positively charged groups on the anion-exchange membranes can include but not be limited to substituted amines. The negatively charged groups on the cation-exchange membranes can include but not be limited to sulfonic or carboxylic acid groups. The ion-exchange membranes must also not adsorb components of the solution mixture to such an extent that fouling of the ion-exchange membranes and significant electric polarization would occur. These membranes are e.g. prepared from fluorinated polymers (polytetrafluoroethylenes), which constitute the polymeric backbone; representative brands are Selemion ®, Nafion ®, Neginst ®, RAI ®, Ionics ® or Ionac ®.

These ion-exchange membranes prevent the passage of acid and base formed at the anode and cathode respectively from passing into the flow passages containing the protein mixture. This is a significant advantage over previous forced-flow electrophoresis units as it allows much lower buffer strengths and hence lower conductivities to be used during the separation, hence lower currents to maintain a needed field strength.

Electric contact is maintained between the electrodes and the ion-exchange membranes by a high conductivity salt solution which is continuously recycled. The high conductivity salt solution should be one which does not contain charged acid or base species which would otherwise permeate through the ion-exchange membrane and change the pH in the separation chambers. A good example of such an electrolyte would be sodium or potassium nitrate. Chloride salts could also be used though they are more corrosive to the electrodes. This electrolyte solutions may be kept separate or allowed to flow from one electrode compartment to the other to neutralize the acid and base formed during a run. In a preferred embodiment of the invention, the electrode chambers and flow passages are filled with a grid to hold the ion-exchange and micro-ultrafiltration membranes in place while enhancing mass transfer.

The hydraulic permeability and other properties of the microporous membrane are determined by the necessity of retaining on the high pressure side of the membrane those charged macromolecular species which are not to be swept over to the permeate side by the liquid flow through the membrane. In particular the local liquid velocity ($V_{liq}$) must not exceed the local electrophoretic velocity ($V_{ep}$) of the least mobile component to be retained. This can be expressed by the equation $$V_{liq} \leq \min|V_{ep}|_{(i')} = \min|-V_{ep}|_i \qquad (2)$$

in which the direction towards the membrane is taken as positive, where $V_{epi}$ is the electrophoretic velocity of the component i. It is negative for retained species. (i') refers to all retained species.

The liquid velocity is composed of two components, one due to the pressure gradient and one arising from the presence of an electric field:

$$\bar{V}_{liq} = \underset{\text{(pressure driven)}}{L_p \Delta \bar{P}} + \underset{\text{(electroosmotic flow)}}{u_e^m \bar{E}} \qquad (3)$$

where Lp is the membrane permeability and $u_e^m$ is the electroosmotic coefficient of the membrane and E is the electric field. If the electroosmotic flow in equation (3) is greater than the allowed value of $\bar{V}_{liq}$ then the pressure must actually be applied in the direction opposite of the liquid flow to partially counterbalance this electroosmotic flow. The electrophoretic velocity is given (cf. equation (1)) by:

$$\bar{V}_{ep} = u_i \bar{E} \qquad (4)$$

where $u_i$ is the electrophoretic mobility of the component i. The field is related to the conductivity of the solution (K) and the current density (i/A) by the equation:

$$\bar{E} = \frac{\bar{i}}{AK} \qquad (5)$$

Equations (3) and (4) can be combined to give the following requirement of the permeability (Lp) of the membrane:

$$L_p \Delta \bar{P} \leq -(u_i u_e^m)\bar{E} \qquad (6)$$

If the electroosmotic coefficient is of the opposite sign as the electrophoretic mobility of the retained species, then the limit on membrane permeability for a given applied pressure is lower in the presence of electroosmotic flows.

Based on these considerations the following operative requirements of the membrane can be defined:

The micro- or ultrafiltration membrane must be highly porous and fairly homogeneous so that the local and average liquid velocities are the same. Since the balancing of the liquid flux and electric field is based on measurement of the total permeation rate divided by the membrane area, there is an implied assumption that the local and average permeation rates are nearly equal. This would rule out sparsely porous membranes.

The hydrodynamic permeability of the membrane must be adapted to fit the electrophoretic velocity of the retained species as explained above. For example, it is not practical to use a membrane requiring control of pressure differences to less than about 0.5 kPa. The range of the membrane pore size may lie within 0.05 to 10 $\mu$m. The lower limit would be that the pores be not so small as to cause sieving effects for any of the macromolecular components which are to be separated on the basis of charge. Since some proteins could have weights up to a few millions, this means having a pore size not below about said 0.05 $\mu$m (50 nm).

Electroosmotic flows of the membrane must not be greater than can be practically controlled by a back pressure control valve. Given the cell geometry, structure, and recycle rates under consideration, a back pressure of 100 kPa is practical maximum. Therefore the limit on the electroosmotic coefficient on a particular membrane is given by rearranging equation (3) and setting $\overline{V}_{liq}$ equal to zero to give:

$$\frac{u_e^m}{L_p} \leq \frac{-\Delta P}{E} \qquad (7)$$

where $\Delta P$ is the applied backpressure to counteract the electroosmotic flow. Note that the left-hand side of the equation is an expression solely in terms of membrane properties and the right-hand side is solely in terms of operating parameters of the forced-flow membrane electrophoresis device.

For a numerical example ($L_p < 10^{-3}$ cm/sec, P < 100 kPa, E < 100 V/cm) the membrane must have an electroosmotic mobility of less than $10^{-3}$ cm$^2$/Volt sec. This is not a very stringent requirement given that protein electrophoretic mobilities are of the order of 0.5 to $5 \cdot 10^{-5}$ cm$^2$/Volt sec.

In order to reduce the chance of electroosmotic and sieving effects, the membrane should have little or no interaction with components in the mixture to be separated. Especially there should be little or no adsorption of protein. Also to minimize electroosmotic effects, the membrane should have few or no charged groups on the pore surfaces, or at least those which cannot be avoided should be homogeneously distributed in the membrane.

To summarize, the preferred properties and ranges of membranes and operating conditions for separation proteinaceous mixtures are:

Electric field: 40-several 100 V/cm (e.g. 40 to 500 or 40 to 300 V/cm)

Pressure: −100 to 100 kPa.

Electrophoretic mobility: 0.5 to $5 \cdot 10^{-5}$ cm$^2$/Volt sec.

Membranes of the following properties can be used: Hydrophilic membranes : such as membranes of polyacrylonitriles, cellulose, acetates, other cellulose esters, hydrophilic polysulfone, or polyamides, or nonadsorbing membranes with no charged group, such as membranes on the basis of polytetrafluoroethylenes.

Their pore sizes may be in the range of 0.05 to 10 $\mu$m and permeabilites are preferably less than about 3600 l/m$^2$·h·bar.

These membranes may be symmetric or asymmetric with the tight side facing towards the feed or towards the permeate side.

Figure 2:
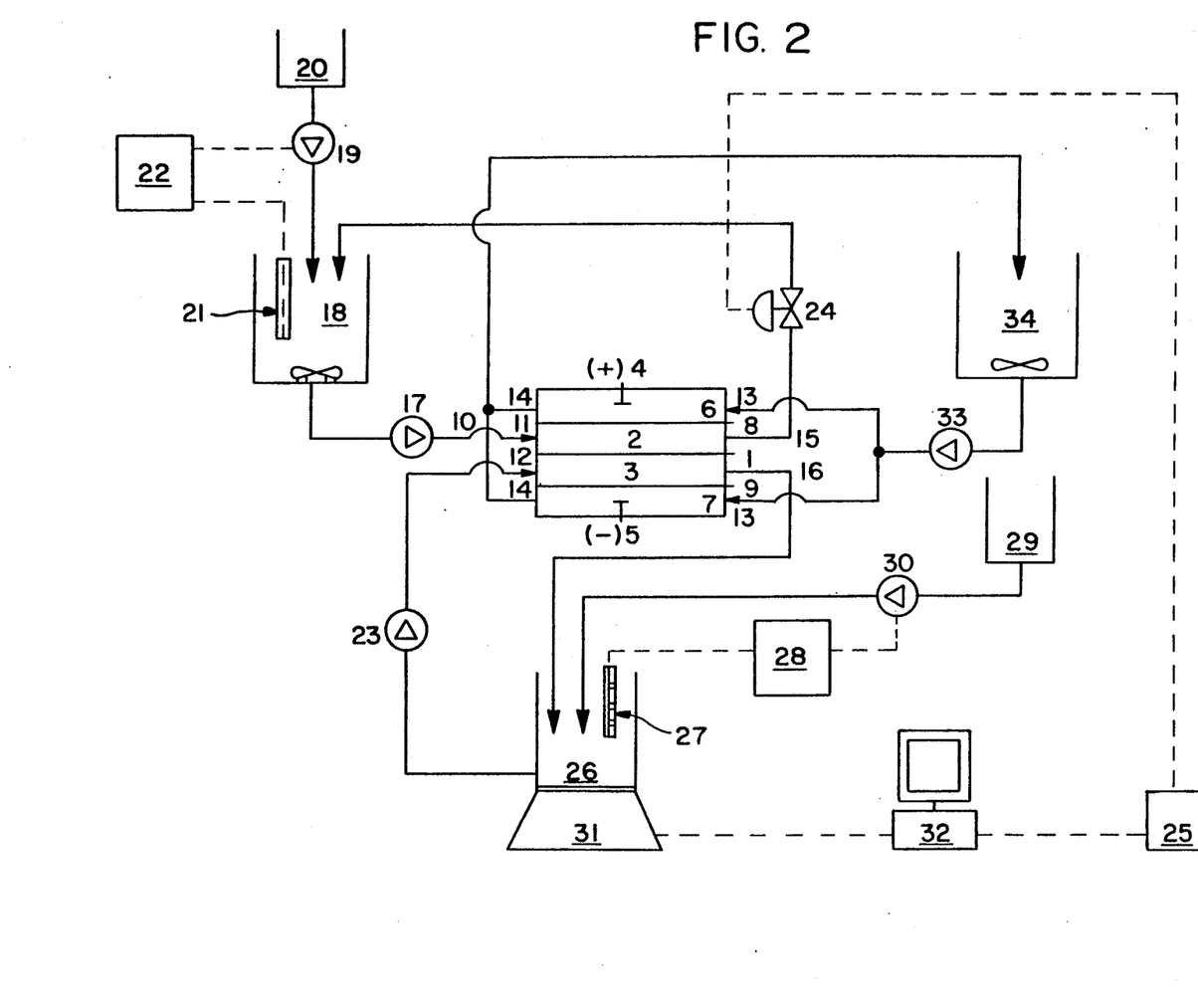
FIG. 2 is a schematic diagram of an inventively used electrophoresis separation device and its supporting equipment.

Referring to FIG. 2, the feed solution (10)—prepared in a feed tank (18) by pumping (19) an aqueous buffer solution from a tank (20) and controlling this addition by a pH-electrode (21) and a pH-controller (22)—is pumped (17) under pressure (pressure driven membrane treatment) to flow tangentially along the high pressure side (feed cell 2) of the microporous membrane membrane while an electric field (anode (4) and cathode (5)) is applied perpendicular to the membrane. This circulation flow of the feed parallel to the membrane keeps the membrane free of gel-polarized material and allows the permeate flux to be maintained. As permeate passes through the membrane (1) only those components which are not charged or have an electrophoretic velocity in the same direction as the permeate flux will be completely transferred to the permeate side (3). The permeate can then flow out of the cell where it is collected under the flow generated by the applied pressure. The flow rate of the permeate can be adjusted by pressure to a predetermined value. In a preferred embodiment a second pump (23) circulates permeate buffer solution to sweep the permeate side of the membrane and collect the permeated molecules. This second arrangement has the advantage of reducing the electric polarization on the low pressure side and reducing the applied voltage needed to maintain a given field strength. Additional ways to reduce the electric polarization are by including a turbulence promoting grid in both the feed and permeate flow passage.

The flux through the membrane must be maintained at a low enough level that the flow velocity towards the membrane does not exceed the electrophoretic velocity away from the membrane of the components to be retained on the feed side. This is effected by controlling a back pressure valve (24) either manually or by an automatic controller (25). In order to measure the flux in the absence of permeate recycle, any flow indicator accurate in the range of the fluxes used (e.g. 1 to 4 cm$^3$/cm$^2$·sec) is adequate. In the presence of a permeate recycle, another method for measuring the net accumulation of permeate on the permeate side must be used as the recycle rate can be more than 100 times and as much as e.g. 1000 times greater than the permeation rate. The residence time of the solutions in the feed/permeate cells is very short, that is in the order of seconds, e.g. 0.1 to 10 seconds.

In one embodiment of this system a weigh scale (31) is used on which the permeate reservoir (26) sits which is equipped with a pH-electrode (22) connected to a pH-controller (28), which effects the controlled addition of buffer solution from tank (29) through pump (30). The net accumulation is measured as a net change in weight. This may be automatically or manually monitored, and in one preferred embodiment is automatically recorded and permeation rates calculated on a microcomputer with monitor (32). This can then be the input to the automatic controller.

The pH of the feed solution is regulated by use of a buffer system with or without external pH control (18, 19, 20, 21, 22).

For the electrolyte circulation and electrode washing the electrolyte solution/washing liquid is pumped (pump 33) from tank (34) through the anode and cathode compartments (6) and (7) and recycled.

The device according to FIG. 2 can be combined (in series) with one or more other (identical) devices wherein steps (a) to (e) of the inventive process can be carried out by differently adjusting the pH-value of the aqueous solutions containing the mixtures of the electrically charged macromolecular compounds. A target compound (protein) can thus be purified by sequentially separating it from the (protein) molecules with pI's higher (lower) than the pI of the target protein, and then from those proteins with pI's lower (higher).

The device can be upscaled all three geometric forms by increasing the membrane area according to the following approaches:

Tubular—Increase the length and the number of tubes per module based on modifications of existing technologies for multitubular membrane filtration devices.

Flat Sheet—Make larger area cells and stack cells with electrodes for each cell pair.

Spiral wound—Increase the diameter and length of the spiral wound unit.

The overall strategy involves using buffer materials with high buffer capacity and low equivalent conductivity in order to preserve the process fluid pH-value while maintaining a low conductivity and hence a high field strength. An example of these kinds of buffers are those developed by Good (Good et al., Biochemistry 5, 467 (1966)). These are amphoteric zwitterionic substances of the buffer type HA/A-. Most of these contain a substituted amine group providing the positive charge and a sulfonate or carbonate group providing the negative charge ($R'R''^H \oplus NRSO_3 \ominus$ or $R'R''^H \oplus NRCOO \ominus$).

An example is the material N-morpholinoethane sulfonate (MES) of molecular structure:

A 2 mM solution of this salt at pH=5.5 has a specific conductivity of only ~40 μmho/cm while a 1 mM solution of a phthalate solution at the same pH has a specific conductivity of 110 μmho/cm. Additional pH control can be supplied by putting a pH controller on the feed or both feed and permeate sides of the electrophoretic cell (not shown in FIG. 2).

If the buffer material is expensive or the target molecule is desired in concentrated form then the permeate can be recycled through a separation device (e.g. an adsorption column, ion exchange membrane or any membrane type concentrating device such as ultrafiltration, etc.) to remove the proteins from the permeate, and return the stripped permeate to the feed to diafilter the feed and push out either the target molecule or contaminants.

Figure 4:
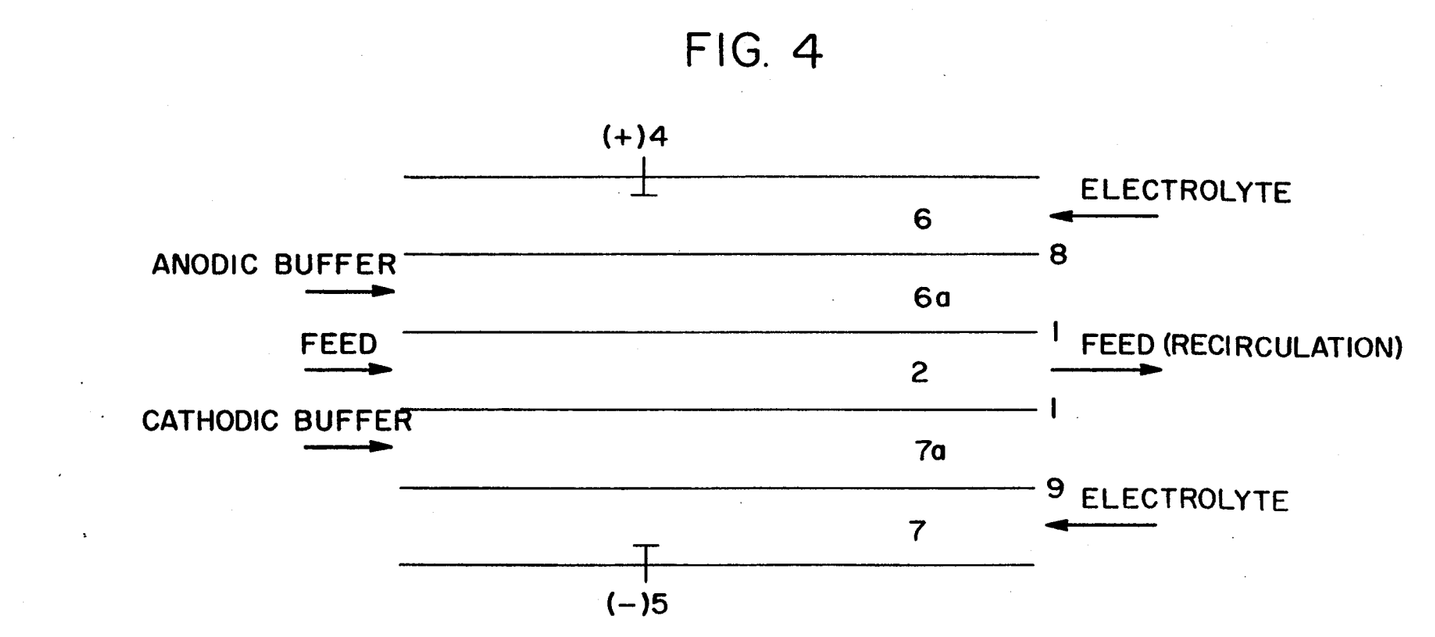
FIG. 4 shows a modified forced-flow membrane electrophoresis scheme, viz. two electrophoresis stacks, piggy-backed one on the top of the other.

One further object of the present invention relates to the principal process for the separation of an electrically charged macromolecular compound by forced-flow membrane electrophoresis, which comprises the simultaneous purification of said macromolecular compound from an aqueous mixture of other charged macromolecular compounds with pI-values both greater and less than that of the macromolecular compound to be separated, in a forced-flow membrane electrophoresis apparatus of two stacks, piggy-backed one on the top of the other, comprising a membrane compartment of a feed cell (2) flanked by an anodic buffer cell (6a) on one side and a cathodic buffer cell (7a) on the other, both being partitioned from the feed cell (2) by micro- or ultra-filtration membranes (1) which are permeable to electrically charged macromolecular compounds, and electrode compartments (6, 7) spaced from each other and having the anode (4) and cathode (5) located therein, being partitioned from the anodic and cathodic buffer cells (6a, 7a) by an anion- and cation-exchange membrane (8, 9) respectively, which are impermeable to said electrically charged macromolecular compounds, and having no or very low permeability to salts.

More particular this process comprises maintaining the pH of the aqueous mixture of charged macromolecules at a value equal to the pI of the macromolecules to be separated and recycled in the feed cell, keeping the pH of the buffer solution in the anodic buffer cell (6a) slightly lower than the pI of the macromolecule to be separated, and the pH of the buffer solution in the cathodic cell (7a) slightly higher than said pI, applying an electric field to cause migration of positively charged macromolecules from the feed cell (2) into the cathodic buffer cell (7a) and of negatively charged macromolecules from the feed cell (2) into the anodic buffer cell (6a), and retaining the macromolecules to be separated in the feed cell (2).

The above embodiments of the present invention, when used in combination with each other, enable to achieve very sharp separation (differences of the isoelectric points of the electrically charged macromolecular compounds in the range of 0.1 to 0.2) which could not be demonstrated by means of previous designs. They serve to achieve the following physical conditions essential to the separation process:

Prevention of leakage of acids and bases formed at the electrodes from entering the (membrane) cells and changing the pH's of the feed mixture, thereby lowering the buffer requirements.

High field intensities within the separating cells and not in the electrode compartments, thus minimizing the Joule-heating effects, which interfere with the separation process. This can be achieved as a result of the use of ion-exchange, salt impermeable membranes at the electrode/separating cell bounderies. The use of such membrane enables to keep electrolyte concentrations in the electrode cells at very high values, and those in the colloid compartments very low. The result is that the main voltage drop occurs through the colloid compartments only where the high field intensity is in effect required.

Reduction of electric polarization in the electrophoretic cell.

Use of optimized buffer systems of high capacity and low conductivity (zwitterionic buffer, also named Good's buffer).

Maintenance of a homogeneous pressure differential across the membrane at each point in the cell, thus maintaining constant linear velocities of the permeating fluid across the cell. As a result the net migration velocity of selected species is homogeneous over the whole cell volume and the separations is sharpened. This is accomplished by having permeate and feed solutions flow at the exact same recycle rate in parallel direction through their respective sides of the separation cell. Given identical geometry for both sides of the separation cell, the pressure drop from inlet to outlet will be the same on both high and low pressure sides.

Maintenance of the net transverse velocity of the permeating species at a predetermined value needed for best separation efficiency. This is accomplished by applying backpressure in the separation device according to computerized feedback to compensate for electroosmotic flow effects which would cause the net transverse velocity to deviate from its required value.

The maintenance of the constant transverse velocity is especially difficult at high field intensities applied to low conductivity solutions. The variations in conductivity can then significantly affect the electroosmotic flow causing instabilities in the rates of permeation of the various molecules thereby reducing the sharpness of separation. Thus, on line recording of permeation rate and feedback corrections of the applied pressure during separation are essential elements of sharp separation capability.

The best flow regime in the feed and permeate compartments, which will contribute to the required local flux homogeneity would be a parallel flow, contrary to the usual coutercurrent flow regime.

The here presented process and device incorporate one additional important and advantageous feature. By having independent control of pH in the feed and permeate compartments, the pH on the feed and on the permeate sides can be maintained at different values. In known isoelectric focussing and free flow electrophoretic devices, there is nothing to prevent diffusive broadening at the boundary between two regions of different pH, except for the inherent buffer strength in that region.

In the device described here the use of high circulation flow and turbulent promoting grids afford rapid mixing on either side of the microporous membrane. As a result the pH on each side is maintained at a uniform value right up to the membrane solution boundary. This generates a very steep pH-gradient across the thickness of the membrane. This is illustrated schematically in FIGS. (3a) and (3b). This can be exploited in the following manner.

FIG. 3a

Two electrically charged components A and B having pI(A)>pI(B) are in the feed solution at pH>=pI(A) and with the permeate side swept by a feed solution at pI(A)>pH(perm)>pI(B). If the field is applied with the anode (4) on the feed side (2) and the cathode (5) on the permeate side (3), the component(A) will reach the membrane (1) but the component (B) will not or at a much lower rate since its electrophoretic velocity will be away from the membrane and greater than A's. However once a molecule of (A) reaches the membrane (1) it passes to a region of pH<pI(A), the molecule's charge reverses and it is accelerated through the membrane at a higher rate than the liquid flow while molecule (B) is still retarded.

FIG. 3b

Alternatively, if pH(perm)>pI(A)>pH(feed)->pI(B), then a molecule of (B) passing through the membrane due to fluctuations of pressure and liquid transverse velocity will be retarded by the higher pH on the permeate side which increases its electrophoretic velocity back towards the feed side. Thus contamination of (A) in the permeate by (B) is further prevented. $V_A$ a $V_B$ are the electrophoretic velocities of components A and B; $V_{liq}$ is the liquid velocity.

FIG. 4

Shows a schematic view of two forced-flow membrane electrophoresis stacks, piggy-backed one on top of the other. The feed cell (2) is in the center and is flanked by an anodic buffer cell (6a) on one side and a cathodic buffer cell (7a) on the other. The contaminants are pushed out on both sides while retaining the feed in the feed cell (2). This has the added advantage of keeping the protein away from the electrode compartments (6, 7) where electric potentials are at extremes. (1) refers to microfiltration or ultrafiltration membranes and (8) and (9) indicate anion- and cation-exchange membranes, respectively, of the type as hereinbefore described).

In order for such a system to work, retention of the main protein in the feed cell (2) requires high fields and appropriate pH-conditions in the bordering buffer cells (6a, 7a). This is so that any main protein carried into the buffer cells (6a, 7a) by convection becomes charged and hence pushed back into the center. In the feed cell (2) the main protein must have a low electrophoretic velocity. Otherwise it will be swept in one direction or the other into one of the buffer cells (6a, 7a). In addition, low conductivity in the feed cell (2) itself generates a high electric field which adds to the flow field in pushing the contaminating proteins out of the feed. Therefore the optimal conditions for such a device are:

low conductivity in the feed and the buffer cells,
pH~pI main protein in the feed cell,
pH=pI of the nearest anodic contaminant in the anodic buffer cell (6a) (pH<pI of the main protein).
pH=pI of the nearest cathodic contaminant in the cathodic buffer cell (7a) (pH>pI of the main protein).

The following examples are presented to exemplify preferred embodiments of the invention and should not be construed as limitation thereof. Parts and percentages are by weight if not indicated otherwise.

EXAMPLE 1

The first set of examples uses the cylindrical form of the device (cf. FIG. 2) with an anode as the central electrode and the cathode as the outer electrode formed by a porous stainless steel support tube. It has an overall length of 24 cm and an inside diameter of 1.27 cm. The anode is separated from the electrophoretic chamber by an anionic exchange membrane. This membrane prevents the acid formed at the anode from passing into the annular electrophoretic flow passage. An electrode solution of 0.5M $NaNO_3$ is pumped over the anode to maintain electric contact between the anode and the anionic exchange membrane. A microporous membrane with pore size of 0.2 micron and net area of 95 $cm^2$ rests against the outer cathode. The annular flow passage defined is 24 cm long with thickness of 0.485 cm.

The feed solution is a mixture of proteins pumped at a flow rate of 1.5 to 2.1 l/min along the flow passage under an applied pressure of 4 to 8 kPa. The pH of the feed is maintained at a set value by a buffer. Liquid permeated from the high pressure side through the microporous membrane and through the cathode to a permeate collection point outside the device. The compositions of feed and permeate are determined spectrophotometrically for the proteins and by a colorimetric reaction for the dextran. In this example the current applied is 0.1 A and the voltage across the cell ranges from 100 to 300 volts.

a. A mixture of myoglobin (pI=7.35(6.85 of minor component)) and bovine serum albumin (BSA)

(pI=4.9) is circulated in a phosphate buffer maintained at pH 6.65 to 6.8 with specific conductivity of 18 μmho/cm. The feed composition is 227 ppm of myoglobin and 950 ppm of BSA. When a current of 0.1 A is applied across the flow passage, the permeation rate of buffer solution across the membrane is 187.5 l/m²·h. The collected permeate has a composition of 488 ppm myoglobin and 0 ppm of BSA. The higher concentration of myoglobin in the permeate is due to it being charged positively (pH<pI myoglobin) so that its electrophoretic velocity caused it to move faster across the membrane than the permeate solution as a whole.

b. A mixture of cytochrome C (pI=10.25) and ovalbumin (pI=4.7) is circulated in a phosphate buffer as in example (1a). The feed composition is 100 ppm of cytochrome C and 400 ppm of ovalbumin. When a current of 0.1 A is applied across the flow passage, the permeation rate through the microporous membrane is 214 l/m²·h. The permeate contained 222 ppm cytochrome and 0 ppm ovalbumin.

c. A mixture of dextran (MW 275000) and myoglobin (pI=7.35) is recycled in a Tris-buffer maintained at pH=9.0 with a specific conductivity of 24.2 μmho/cm. The concentration of the dextran is 988 ppm and the concentration of the myoglobin is 150 ppm. Before the field is applied the permeate composition is 988 ppm dextran and 96 ppm myoglobin with a flux of 33 l/m²·h. On applying a current of 0.1 Ampere across the flow passage, the flux increases to 172 l/m²·h and the permeate composition becomes 924 ppm dextran and 0 ppm myoglobin.

EXAMPLE 2

This example uses the same apparatus as in Example 1. The microporous membrane is a supported polyacrylonitrile membrane with a pore size of 0.45 micron.

A mixture of alpha-amylase (98 ppm) (pI=5.2 to 5.4) and myoglobin (89 ppm) (pI=7.35) is the feed solution. The enzymatic activity of alpha-amylase and the total protein content are determined by the method of P. Bernfeld—Enzymatic activity of α-amylase, Methods in Enzymology, 1, 149 (1955) and the modified Lowry method for protein analysis according to Ohnishi and Barr, Anal. Biochem. 86, 193 (1978).

The pH-value of the feed is maintained at 6.8 using a phosphate buffer diluted to an initial conductivity of 34 μmho/cm. At the beginning of the experiment the alpha-amylase has an activity of 92100 units ml and total protein is 171 ppm. When a voltage of 95 V is applied across the cell the flux through the membrane is 95 l/m²·h and the permeate contains 108 ppm total protein but only 2460 units of enzyme activity (97% rejection of enzyme).

EXAMPLE 3

Figure 1:
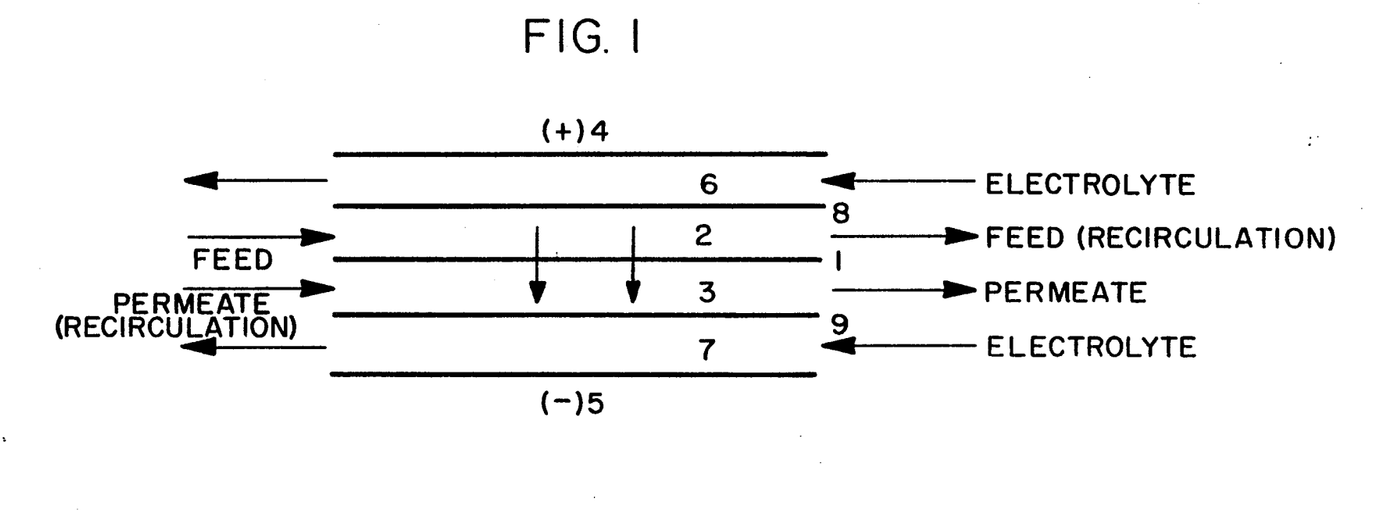
FIG. 1 is a schematic view of the forced-flow membrane electrophoresis.

A flat electrophoresis apparatus shown in FIG. 1 is used with upper and lower electrophoretic flow cells separated by a 0.45 μm microfiltration membrane of 30 cm². Each cell is 3 mm thick by 3 cm wide by 10 cm long. The fluid inlet and exit ports are at the ends of the long dimension of the cells.

The anode at the top and the cathode at the bottom of the device are separated by anion and cation exchange membranes (Selmion ®), respectively. A turbulence promoting grid is provided in both the top and bottom flow cells of the membrane compartment. As shown in FIG. 2, two pumps are used to circulate sample and buffer along the top and bottom surface of the microfiltration membrane with an overpressure on the fluid flowing along the top surface of the membrane. A third pump is used to recycle 0.5M NaNO₃ electrode solution across the anode and cathode and maintain electrical contact with the ion-exchange membranes. The recycling of the same electrode solution through both cathode and anode promoted neutralization of the base and acid formed in the respective electrode compartments. Current measurements show that there is only a small portion of the current flowing through the electrode solution.

a. A commercial sample of horse myoglobin (Sigma Cat. No. M1882) is placed on the feed side. It has a series of pI bands ranging from 5.1 to 8.0 (see Table 1). The 500 ppm solution of this sample is recirculated at a pH of 7.25 to 7.35 using a 2 mM MES buffer solution with specific conductivity of 105 μmho/cm.

On applying a field of 0.1 A and 60 V (field strength of 32 V/cm) a permeate is obtained at the rate of 3.0 ml/min. Ultrathin isoelectric focussing gels (dimension of the isoelectric focussing device: 20.5×14.5 cm; electric field parallel to the short side) are run on feed and permeate samples using loadings of 2.5 μgs total protein per sample and silver stained using the procedure of Heukeshoven and Dernick (Electrophoresis, 6, 103–112, 1985). All of the bands with pI below 6.8 are eliminated (bands 6 to 11 in Table 1).

TABLE 1

Position of horse myoglobin bands on the isoelectric focussing gel.

| No. of band | pH-value | distance from cathode (cm) |
|---|---|---|
| 1 | 8.0 | 0.2 |
| 2 | 8.0 | 0.55 |
| 3 | 7.55 | 1.7 |
| 4 | 7.45 | 1.8 |
| 5 | 7.0 | 2.5 |
| 6 | 6.8 | 3.6 |
| 7 | 6.6 | 4.7 |
| 8 | 6.3 | 5.6 |
| 9 | 6.05 | 7.4 |
| 10 | 5.3 | 8.7 |
| 11 | 5.1 | 8.9 | b. An apparatus as in Example (3a) is used. A partially purified sample of the proteinase inhibitor Eglin (pI=5.5 at 4° C.) containing 500 ppm (based on UV-absorbance at 277 nm) is recycled on the feed side which is next to the anode. The pH is maintained at 5.2 on the feed side and 5.35 on the permeate side using a 0.2 mM solution of MES as the buffer. The initial conductivity is 30 μmho/cm. A current of 0.1 A is applied generating a field of 110 V/min.

The permeate pH is allowed to go up to 6.5 while the feed pH is maintained at 5.2. The permeate rate is maintained at 0.7 to 1.2 ml/min.

An ultrathin isoelectric focussing (UTLIEF ®)-gel of the permeate and the original feed are run at a loading of 10 μg total protein each sample and silver stained. It can be seen (Table 2) that the impurity bands are removed from the permeate to within a pH of 0.15 of the main protein.

TABLE 2

| | pH-value of bands on gel | |
|---|---|---|
| No. of band | feed | permeate |
| 1 | 4.63 | |
| 2 | 4.7 | |
| 3 | 4.78 | these bands are |
| 4 | 4.82 | |

TABLE 2-continued

| No. of band | pH-value of bands on gel | |  |
|---|---|---|---|
|  | feed | permeate |  |
| 5 | 4.9 | removed |  |
| 6 | 5.05 |  |  |
| 7 | 5.25 | 5.25 |  |
| 8 | 5.28 | 5.28 |  |
| 9 | 5.39 | 5.39 | (main band) |
| 10 | 5.55 | 5.55 |  |
| 11 | 5.82 | 5.82 |  |
| 12 | 6.35 | 6.35 |  |
| 13 | 6.46 | 6.46 | these bands are enhanced relative to feed |
| 14 | 6.78 | 6.78 |  |
| 15 | 6.8 | 6.8 |  |
| 16 | 6.85 | 6.85 |  |
| 17 | 7.85 | 7.85 |  | c. As in Example (3b) except that the Eglin solution is fed next to the cathode. The initial feed solution conductivity is 45 μmho/cm and the applied current is 0.2 A (148 V/cm). Using a buffer system of MES/HCL with an initial MES concentration of 2 mM, the system maintained at pH 5.5 on the feed side and 5.6 on the permeate side. The permeate rate is 0.8 ml/min for four hours. Analysis of removal of impurities is done as in Examples (3a) and (3b) using UTLIEF ® gels. As seen in Table 3, all of the impurity bands more basic than 0.2 pH units of the main band are removed except for two at pH=6.78/6.8. Titration curves showed that these components have extremely flat titration curves so that their electrophoretic mobilities at pH=5.6 are still extremely low and therefore little affected by the electric field.

TABLE 3

| No. of band | pH-value of bands on gel | |  |
|---|---|---|---|
|  | feed | permeate |  |
| 1 | 4.63 | 4.63 |  |
| 2 | 4.7 | 4.7 |  |
| 3 | 4.78 | 4.78 |  |
| 4 | 4.82 | 4.82 | these bands are enhanced relative to feed |
| 5 | 4.9 | 4.9 |  |
| 6 | 5.05 | 5.05 |  |
| 7 | 5.25 | 5.25 |  |
| 8 | 5.28 | 5.28 |  |
| 9 | 5.39 | 5.39 | (main band) |
| 10 | 5.55 | 5.55 |  |
| 11 | 5.82 |  |  |
| 12 | 6.35 |  | removed bands |
| 13 | 6.46 |  |  |
| 14 | 6.78 | 6.78 |  |
| 15 | 6.83 | 6.8 |  |
| 16 | 6.85 |  | removed bands |
| 17 | 7.85 |  |  |

EXAMPLE 4

As illustrated in FIG. 4 a modified version of the device in Example 3 is used. In this modified device, the electrophoretic chamber is divided into three flow cells [feed cell (2); anodic buffer cell (6a); cathodic buffer cell (7a)] by microfiltration membranes (1) of 0.1 μm cutoff and area of 30 cm². As in the device in Example 3, each flow cell is 3 mm thick by 3 cm wide by 10 cm long. The fluid inlet and exit ports are at the ends of the long dimension of the cells. Turbulence grids (not shown) are provided in all three flow cells as well as in the electrode wash compartment (6, 7). As in the device in Example 3, the anode (4) and cathode (5) are separated from the electrophoresis cell by an anion exchange (8) and cation exchange (9) membrane, respectively. Electrical contact between the electrodes and the ion exchange membranes is maintained as described in Example 3.

The feed sample is circulated through flow cell (2) and buffer solutions are circulated through flow cells (6a and 7a) at 300 to 500 ml/min with a pump for each recycle loop. The feed sample pH is maintained at or near the pI of the protein to be purified while the buffer solution in chamber (6a) is maintained at several tenths of a pH unit lower and the buffer solution in chamber (7a) is maintained at several tenths of a pH unit higher by external pH controllers (22 in FIG. 2) on each recycle loop.

A simple buffer system such as N-morpholino-ethane sulfonic acid (MES) and its sodium salt is used in all three flow cells. Backpressure valves and flow controllers (24 and 25 in FIG. 2) on the outside flow cells (6a and 7a in FIG. 4) prevent or provide a controlled net transfer of liquid between the outside flow cells and the central feed cells (2 in FIG. 4).

A solution of partially purified Eglin (pI=5.5) is recycled in the central flow cell (2) for four hours. The initial and final conditions in the three flow cells is shown in Table 4. The field tended to push the contaminants out to the outer flow cells (2a, 6a) while causing the target protein to be retained in the central cell (2). This is shown by an isoelectric focussing gel test of the sample solution in flow cell (2) at the beginning and the end of the run. These gels are run at a loading of 10 μg total protein per track and silver stained. As can be seen in Table 5, impurity bands are removed from both sides of the protein to within 0.2 pH units of the main protein.

TABLE 4

| Performing conditions | | | | |
|---|---|---|---|---|
|  | Sample | Conductivity (μmho/cm) | pH | |
| START | anode buffer | 24 | 5.31 | I: 100 mA U: 275 V |
|  | feed | 10 | 5.51 |  |
|  | cathode buffer | 120 | 5.82 |  |
| FINISH | anode buffer | 46 | 5.28 | I: 100 mA U: 250 V |
|  | feed | 6 | 5.5 |  |
|  | cathode buffer | 620 | 5.83 |  |

TABLE 5

| No. of Band |  | pH-values of band on gel | |
|---|---|---|---|
|  |  | FEED sample loading 10 μg on gel | PRODUCT sample loading 10 μg on gel |
| 1 | strong | 4.63 | removed |
| 2 |  | 4.7 | removed |
| 3 | strong | 4.78 | removed |
| 4 |  | 4.84 | almost all removed |
| 5 |  | 4.88 | removed |
| 6 |  | 4.95 | almost all removed |
| 7 |  | 5.15 | almost all removed |
| 8 |  | 5.29 | significantly reduced |
| 9 |  | 5.35 | almost all removed |
| 10 | strong | 5.41 | 5.41 |
| 11 | MAIN BAND: | 5.44 | MAIN BAND: 5.44 |
| 12 |  | 5.52 | 5.52 |
| 13 |  | 5.82 | removed |
| 14 | strong | 6.35 | removed |
| 15 | strong | 6.46 | removed |
| 16 | strong | 6.78 | removed |
| 17 | strong | 6.8 | removed |
| 18 |  | 6.85 | removed |

TABLE 5-continued

| | pH-values of band on gel | |
|---|---|---|
| No. of Band | FEED sample loading 10 μg on gel | PRODUCT sample loading 10 μg on gel |
| 19 | 7.84 | removed |

Gel: 6% crosslinked polyacrylonitrile gel (6T/4C)
pH gradient: 4-8 (Pharmalytes ®)
Sample: partially purified Eglin
Area: 30 cm²

We claim:

1. A process for the continuous separation of electrically charged macromolecular compounds by forced-flow membrane electrophoresis, which comprises conducting said process in an electrophoretic cell comprising
    (1) a membrane compartment consisting of a feed and a permeate cell which are divided by a micro- or ultrafiltration membrane permeable to said macromolecular compound,
    (2) electrode compartments which comprise anode and cathode compartments at opposite sides of the membrane compartment
    (1) which are partitioned from the cells of the membrane compartment with ion-exchange membranes, wherein the anode compartment is bordering the membrane compartment by an anion-exchange membrane and the cathode compartment is bordering the membrane compartment by a cation-exchange membrane, the ion-exchange membranes being impermeable to said macromolecular compound and having no or very low permeablility to salts, and
    (3) means to control the flow rate to the permeate, by the process steps of
        (a) recycling aqueous solutions containing mixtures of electrically charged macromolecular compounds, and having a pH-value between the isoelectric points of said macromolecular compounds, through said feed cell and subjecting them to a pressure-driven membrane separation treatment,
        (b) simultaneously applying an electric field across the solutions, the micro- or ultrafiltration membrane and the ion-exchange membranes to induce electrophoretic migration of at least one of the macromolecular compounds through the micro- or ultrafiltration membrane or away from all the membranes,
        (c) adjusting the flow rate of the permeate to a predetermined value,
        (d) withdrawing at least one of the macromolecular compounds either from the feed or permeate cell, and
        (e) recycling a dilute buffer solution through the permeate cell to sweep away macromolecular materials which have permeated through the membrane; the dilute solution may be at a pH equal, lower or higher than the pH of the feed solution, the recycle rate in the permeate and feed cells being many times the rate of feed solution-permeation and the residence time of the solution in the cells being very short.

2. A process according to claim 1, wherein the feed and the permeate cell are divided by an inorganic or organic polymeric micro- or ultra-filtration membrane.

3. A process according to claim 1, which comprises carrying out steps (a) to (e) by adjusting the pH-value of the aqueous solutions containing the electrically charged macromolecular compounds first below and then above the isoelectric point of the macromolecular compound to be separated.

4. A process according to claim 1, wherein the pH-value is maintained at the pI of the macromolecule to be separated and subsequently applying the electric field to cause migration first of the positively and then of the negatively charged macromolecules from the feed cell through the membrane while the desired macromolecule is retained.

5. A process according to claim 1, wherein the aqueous solutions are circulated under pressure in the feed and in the permeate cells and the electric field causes the electrophoretic migration of at least one of the electrically charged macromolecular compounds causing it to pass through the membrane into the permeate cell from which it is withdrawn, or to retain it in the feed cell, preventing its passage into the permeate cell.

6. A process according to claim 1, wherein the aqueous solutions are buffered aqueous solutions of optionally colloidal biopolymers.

7. A process according to claim 1, wherein the membrane compartment contains dilute buffer solutions and the electrode compartments highly concentrated electrolyte solutions.

8. A process according to claim 7, wherein the buffers used in the diluted buffer solutions are monovalent species of the type $HA/A^-$ and $HB^+/B$ with a high buffer capacity per unit conductivity.

9. A process according to claim 1, wherein the recycle rate through each cell is more than 100 times greater than the permeation rate.

10. A process according to claim 1 for the continuous separation of an electrically charged macromolecular compound by forced-flow membrane electrophoresis, which comprises the simultaneous purification of said macromolecular compound from an aqueous mixture of other charged macromolecular compounds with pI-values both greater and less than that of the macromolecular compound to be separated, in a forced-flow membrane electrophoresis apparatus of two stacks, piggy-backed one on the top of the other, comprising
    a membrane compartment of a feed cell (2) flanked by an anodic buffer cell (6a) on one side and a cathodic buffer cell (7a) on the other, both being partitioned from the feed cell (2) by micro- or ultrafiltration membranes (1) which are permeable to electrically charged macromolecular compounds, and
    electrode compartments (6, 7) spaced from each other and having the anode (4) and cathode (5) located therein, being partitioned from the anodic and cathodic buffer cells (6a, 7a) by an anion- and cation-exchange membrane (8, 9), respectively, which are impermeable to said electrically charged macromolecular compounds, and having no or very low permeability to salts.

11. A process according to claim 10, which comprises maintaining the pH of the aqueous mixture of charged macromolecules at a value equal to the pI of the macromolecule to be separated and recycled in the feed cell (2), keeping the pH of the buffer solution in the anodic buffer cell (6a) slightly lower than the pI of the macromolecule to be separated, and the pH of the buffer solution in the cathodic cell (7a) slightly higher than said pI, applying an electric field to ease migration of positively charged macromolecules from the feed cell (2) into the cathodic buffer cell (7a) and of negatively charged macromolecules from the feed cell (2) into the anodic buffer cell (6a), and retaining the macromolecules to be separated in the feed cell (2).

12. A process according to claim 1, which comprises carrying out steps (a) to (e) by adjusting the pH-value of the aqueous solutions containing the electrically charged macromolecular compounds first above and then below the isoelectric point of the macromolecular compound to be separated.

13. A process according to claim 6, wherein the biopolymers are proteins.

* * * * *